United States Patent
Kartäusch et al.

(10) Patent No.: US 11,707,236 B2
(45) Date of Patent: Jul. 25, 2023

(54) MONITORING A RESPIRATORY CURVE

(71) Applicant: Siemens Healthcare GmbH, Erlangen (DE)

(72) Inventors: Ralf Kartäusch, Bubenreuth (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 142 days.

(21) Appl. No.: 16/558,603

(22) Filed: Sep. 3, 2019

(65) Prior Publication Data
US 2020/0077962 A1 Mar. 12, 2020

(30) Foreign Application Priority Data
Sep. 11, 2018 (DE) .................. 10 2018 215 415.5

(51) Int. Cl.
*A61B 5/00* (2006.01)
*A61B 5/113* (2006.01)
(Continued)

(52) U.S. Cl.
CPC ............ *A61B 5/7292* (2013.01); *A61B 5/055* (2013.01); *A61B 5/113* (2013.01); *A61B 5/7285* (2013.01);
(Continued)

(58) Field of Classification Search
CPC ....... A61B 5/7292; A61B 5/113; A61B 5/055; A61B 5/7289; A61B 5/7285;
(Continued)

(56) References Cited

U.S. PATENT DOCUMENTS 10,247,804 B2    4/2019  Nielsen
2012/0271155 A1* 10/2012 Stemmer .............. A61B 5/7285
                                                     600/413
(Continued)

FOREIGN PATENT DOCUMENTS

DE    102005034686 A1   2/2007
DE    102015218106 B4   5/2017
(Continued)

OTHER PUBLICATIONS

German Office Action for German Application No. 10 2018 215 415.5 dated Jul. 15, 2019.

*Primary Examiner* — Christopher L Cook
(74) *Attorney, Agent, or Firm* — Lempia Summerfield Katz LLC (57) ABSTRACT

A method is provided for monitoring a current respiratory curve of a patient with regard to a recording region which is imaged by magnetic resonance scanning. The method includes acquiring a reference respiratory curve of the patient over a plurality of respiratory cycles; establishing a respiration state of the patient that is suitable for the magnetic resonance scanning based on the reference respiratory curve; determining at least one reference recording time window and a trigger threshold value for starting a magnetic resonance scan based on the previously determined respiration state; carrying out at least one magnetic resonance scan within the determined reference recording time window of the current respiratory curve using the trigger threshold value; and continually acquiring and monitoring the current respiratory curve during the magnetic resonance scan in the reference recording time window.

18 Claims, 3 Drawing Sheets

(51) Int. Cl.
*A61B 5/055* (2006.01)
*G01R 33/567* (2006.01)

(52) U.S. Cl.
CPC ............ *A61B 5/7289* (2013.01); *A61B 5/742* (2013.01); *G01R 33/5673* (2013.01)

(58) Field of Classification Search
CPC ..... A61B 5/0033; A61B 5/0037; A61B 5/004; A61B 5/11; A61B 5/721; G01R 33/5673; G01R 33/567; G01R 33/20; A61N 2005/1055; G06T 2207/10088
See application file for complete search history.

(56) References Cited

U.S. PATENT DOCUMENTS

| | | | |
|---|---|---|---|
| 2013/0085376 A1* | 4/2013 | Ringholz | A61B 5/055 600/413 |
| 2015/0157277 A1* | 6/2015 | Goto | A61B 5/721 600/413 |
| 2016/0091591 A1 | 3/2016 | Grodzki | |
| 2017/0016972 A1 | 1/2017 | Bhat | |
| 2017/0082718 A1 | 3/2017 | Beck | |
| 2017/0251949 A1 | 9/2017 | Carinci | |
| 2018/0353139 A1* | 12/2018 | Speier | G01R 33/56341 |

FOREIGN PATENT DOCUMENTS

| | | | |
|---|---|---|---|
| DE | 102016203416 A1 | 9/2017 | |
| DE | 102011076882 B4 * | 12/2018 | ........... A61B 5/7253 |

\* cited by examiner

MONITORING A RESPIRATORY CURVE

The present patent document claims the benefit of German Patent Application No. 10 2018 215 415.5, filed Sep. 11, 2018, which is hereby incorporated by reference.

TECHNICAL FIELD

The disclosure relates to monitoring a current respiratory curve of a patient.

BACKGROUND

Magnetic resonance imaging is a widespread technology for generating magnetic resonance images of a body interior of a patient. It relies on the physical phenomenon of nuclear magnetic resonance (MR). It is distinguished by large and variable soft tissue contrasts. For this purpose, with the aid of an MR apparatus, excitation pulses of a pulse sequence are radiated into the patient and initiate MR signals in the patient. The MR signals may be received by MR coils and are passed on to an evaluating unit in order to generate an MR image of the patient from the MR signals. If magnetic resonance data of a patient is recorded in the region of the torso, (e.g., the thoracic and/or abdominal regions), the corresponding recording regions may also be moved by cyclical motions due to the breathing or heartbeat of the patient. This leads to motion artifacts such as "ghosts" or "double edges" corresponding to a multiple imaging of anatomical structures at different positions at different times or a blurring of the anatomical structures.

In principle, two approaches for preventing motion artifacts are known which are also combinable and are both based on the provision of motion information regarding a cyclical motion.

Such motion information may be taken into account already on recording the magnetic resonance data, in that the recording takes place, for example, triggered and/or only within defined recording time windows of the cyclical motion. For the definition of a recording time window, the fact is utilized that the breathing or heart motion repeats at least similarly, as periodic motions. Accordingly, sub-portions may be determined for the motion cycles. Some sub-portions may be suitable for the recording of magnetic resonance data, in particular, the sub-portion of complete exhalation, because this sub-portion is relatively long. At the start of a sub-portion suitable for a measurement, a trigger signal may be generated in order to start the recording of magnetic resonance data.

Alternatively, a computational correction of motion effects in the magnetic resonance data is known. Herein, the motion information is used to identify magnetic resonance data that is not or is only slightly impaired by the movement and/or to minimize the artifacts by a correction algorithm.

Such methods are described in detail, for example, in German Patent Publication No. 102015218106 B4, U.S. Patent Application Publication No. 2017/0016972 A1, and U.S. Patent Application Publication No. 2016/0091591 A1.

These approaches presuppose a more exact acquisition of the periodic motion of the patient. Nowadays, substantially two methods are used: navigator scans or navigators and motion sensors. Both methods generate an item of motion information, in particular, a measurement variable, from which time points and time windows of motion cycles may be derived.

By motion sensors, patient motion is acquired independently of the magnetic resonance imaging. An electrocardiogram (ECG), a respiratory belt, and/or a respiratory sensor integrated into a local coil are examples of such sensors. The measurement methods used each include, for example, the reception of electrical fields (ECG) or the detuning of an oscillation circuit (e.g., respiratory sensor). An advantage of the motion sensors is their independence from the magnetic resonance scan. Motion sensors may thus provide movement data before, during, or after a scan. The motion sensors, however, are arranged in the immediate vicinity of or directly on the body of the patient, with the result that their signal quality is disadvantageously dependent on the positioning of the sensor or the physiology/positioning of the patient. Given unfavorable positioning of the patient or of the motion sensor, a measured respiratory curve may represent, for example, the abdominal breathing although the chest breathing is desired. For particularly large/small patients, motion sensors are substantially unsuitable.

Navigators are extremely rapidly performable MR scans with a navigator sequence which may be carried out before, during (e.g., only in recording pauses), and after the recording of the magnetic resonance data and indicate the motion status of the recording region. Navigators may correspond to one-dimensional scans which reproduce the position of an anatomical structure influenced by the motion. For example, a navigator tracks the position of the diaphragm and/or of the dome of the liver while the patient breathes. The scan result of the navigator sequence, a respiratory curve, may be used to trigger the recording of magnetic resonance data, for example, in the recording time window of the complete exhalation. After the recording time window, the navigator sequence may be played out again, in order to acquire a further respiratory cycle. Navigator scans permit a highly precise acquisition of a respiratory curve, although the initial positioning of the navigator volume, (e.g., by a scout recording), is highly sensitive to unexpected and, in particular, aperiodic patient movement during the course of a scan, (e.g., sneezing or twitching).

Once respiration states, recording time windows, and/or trigger levels are defined for an original respiratory curve, an additional aperiodic patient movement may displace the respiratory curve, or the respiration state selected for the scan, relative to the initially set trigger level, and may even do so unnoticed. If, during the subsequent respiratory cycles, the trigger level is no longer reached, no new scan is started until a "new learning" of the respiratory curve and a new setting of the trigger level at the start of a desired recording window has taken place. However, when the trigger level is achieved in the subsequent respiratory cycles despite the displaced respiratory curve, the recording time window potentially lies at least partially outside the desired respiration state and scanning is carried out over undesirable respiration states. The magnetic resonance images thus generated are then be discarded as unusable.

SUMMARY AND DESCRIPTION

It is an object of the present disclosure to provide alternative methods, devices, systems, etc., which permit the matching of previously defined trigger levels and recording time windows according to a desired respiration state to be checked automatically, reliably, and continuously. In particular, it is an object of the present disclosure, in the event of deviations between the trigger level and the recording time window, to enable early correction measures.

The scope of the present disclosure is defined solely by the appended claims and is not affected to any degree by the statements within this summary. The present embodiments may obviate one or more of the drawbacks or limitations in the related art.

This object is achieved by a method for determining a tissue function of a tissue, a corresponding computation unit and a medical imaging system, a corresponding computer program, and a corresponding computer-readable data carrier.

The solution to the problem is described below, both in relation to the claimed method and also in relation to the claimed devices. Features, advantages, or alternative embodiments mentioned herein are also transferable similarly to the other claimed subject matter and vice versa. In other words, the present claims (which are directed, for example, to a method) may also be further developed with features that are disclosed or claimed in conjunction with one of the devices. The corresponding functional features of the method are thereby provided by corresponding modules or units.

The present disclosure relates in a first aspect to a method for monitoring a current respiratory curve of a patient with regard to a recording region which is imaged by magnetic resonance scanning. The method includes the following acts: acquiring a reference respiratory curve of the patient over a plurality of respiratory cycles; establishing a respiration state of the patient that is suitable for the magnetic resonance scanning based on the reference respiratory curve; determining at least one reference recording time window and a trigger threshold value for starting a magnetic resonance scan based on the previously determined respiration state; and carrying out at least one magnetic resonance scan within the determined reference recording time window of the current respiratory curve using the trigger threshold value.

It is characteristic of the method that the current respiratory curve is continually further acquired and continually monitored during the magnetic resonance scan in the recording time window.

In other words, a current respiratory curve is acquired not only between the individual scans, but also in parallel or simultaneously with the scans. This continuous acquisition of the current respiratory curve advantageously enables a continuous monitoring of its shape. Thus, the disclosure enables an immediate or semi-real time determination that, as a result of a patient motion, in particular, an unforeseen or non-periodic movement, the reference recording time window and/or the trigger threshold value no longer match the current respiratory curve.

A patient is understood in the following as being the examination object, (e.g., a human). In principle, the patient may also be an animal. Therefore, in the following, the two expressions "examination object" and "patient" are used synonymously.

The patient is to be subjected to a magnetic resonance scan and magnetic resonance data is therefore to be acquired by a medical imaging system, in particular, a magnetic resonance tomograph, in a per se known manner. A recording region of the body of the patient is thereby imaged. The recording region is a body part, a body region, or a subregion which is to be imaged by the medical imaging system. In particular, the recording region is a body region of the patient which in the rest position of the patient also carries out a periodic motion, especially a respiratory motion, in particular, the thorax and/or the abdomen. The recording region may thus be any body region, which is also moved by the periodic respiratory motion. A magnetic resonance scan may include one or a plurality of individual scans. The periodic respiratory motion of the patient may be represented and described with motion information in the form of a respiratory curve.

The respiratory curve of the patient may be acquired by a sensor unit which is configured to capture the body motion of the patient caused by breathing. The sensor unit is configured to detect the body motion caused by respiration before, during, between and after magnetic resonance scanning, that is, substantially continuously. The sensor unit may be implemented in a variety of ways making use of different functional methods, as described in greater detail below.

The disclosure distinguishes a reference respiratory curve and a current respiratory curve. The reference respiratory curve may include a plurality of respiratory cycles and serves for the determining, definition and/or establishment of at least one respiration state, reference recording time window and/or a trigger threshold value.

A respiratory cycle includes a complete inhalation and a subsequent complete exhalation by the patient. A respiratory cycle therefore includes different respiration states. In the rest state of the patient, successive respiratory cycles have a great similarity with regard to the shape and duration thereof, so that a respiration state, in particular, complete exhalation may be determined exactly and reliably based on the respiratory curve. A reference respiratory curve may be acquired before or between two individual scans of a magnetic resonance scan. It may include three to five successive respiratory cycles of the patient, but in individual cases may also include more or fewer respiratory cycles, for example, in a patient with per se irregular breathing or if unforeseen patient movement takes place during the acquisition of the reference respiratory curve.

A reference recording time window corresponds to a temporal recording duration within a respiratory cycle, within which magnetic resonance scans may be carried out. The reference recording time window is defined based on at least one previously determined respiration state. Thus, the respiration state of full exhalation is, for example, most suitable for magnetic resonance scans because full exhalation corresponds to a relaxation state of the thorax and may last longer than inhalation. The reference recording time window thus includes the duration of the at least one respiration state, in particular, the respiration state and the reference recording time window are arranged coincident in the course of a respiratory cycle. Alternatively, the reference recording time window may be longer or shorter than the determined respiration state and/or may be set with a temporal offset therefrom. The reference recording time window is used to define the temporal regions in the course of the current respiratory curve according to the desired respiration state, in which a magnetic resonance scan may take place. The reference recording time window has the effect that the magnetic resonance data of a magnetic resonance scan corresponds only to the desired respiration state, whereby motion artifacts are minimized or prevented. The trigger threshold value corresponds to the value of the reference respiratory curve that the reference respiratory curve has at the start point of the reference recording time window. The trigger threshold value may be used to start an individual scan of a magnetic resonance scan. The scan may be started instantly on reaching the trigger threshold value or with a further temporal offset.

A current respiratory curve may also include one or a plurality of respiratory cycles of the patient. It serves for monitoring a patient motion. The current respiratory curve includes, in particular, the respiratory cycles in which magnetic resonance data is acquired within the determined reference recording time window. However, it may also include respiratory cycles in which no magnetic reference scan takes place, and which are not included by the reference respiratory curve. The reference respiratory curve and the current respiratory curve may transition directly into one another beginning with the reference respiratory curve and/or may be interleaved with one another, that is, they may take place alternatingly multiple times.

In an advantageous embodiment, the continuous monitoring of the current respiratory curve includes establishing at least one parameter that is characteristic for the current respiratory curve and checking for matching with the corresponding parameter of the reference respiratory curve. The presence of and/or the extent of a deviation between a parameter relating to the current respiratory curve and the reference respiratory curve may be indicators of a patient movement that has taken place in addition to the respiratory motion. This movement may be the cause of a deviation between reference recording time windows or the trigger threshold value and the shape of the current respiratory curve. The movement may be, for example, an unforeseeable and/or aperiodic motion which may also occur multiple times and, in particular, may be a single movement. This movement may influence both the duration of respiratory cycles, the position or the spacing of extreme points, and/or the shape between adjacent extreme points.

This embodiment therefore represents a comparison between the current respiratory curve and the reference respiratory curve. The comparison advantageously provides information as to whether the shape of the current respiratory curve is similar or comparable to the shape of the reference respiratory curve. This embodiment therefore enables determination of whether the trigger threshold value and/or the reference recording time window still match the desired respiration state. Just one or a plurality of parameters of the current respiratory curve may be monitored. The comparison may take place based upon absolute or relative values of the at least one parameter.

In another development, the continuous monitoring of the current respiratory curve includes establishing at least one parameter that is characteristic for a first respiratory cycle of the current respiratory curve and checking for matching with the corresponding parameter of a second respiratory cycle of the current respiratory curve. An unforeseen movement may also thereby be detected in that individual respiratory cycles of the current respiratory curve are compared based on at least one parameter. It is particularly advantageous if a comparison takes place for one or more parameters both against the reference respiratory curve and another respiratory cycle of the current respiratory curve.

According to a particular embodiment, the at least one parameter is a parameter from the group of the following parameters: the position of at least one turning point (in particular, an extreme point) of the current respiratory curve, a temporal spacing of two successive turning points of the current respiratory curve, a spacing between minimal and maximal deflection of a respiratory cycle of the current respiratory curve, the gradient and/or the constancy of the current respiratory curve.

The continuous monitoring of the current respiratory curve may advantageously also include placing at least one parameter of the current respiratory curve in relation to the reference recording time window. In other words, the disclosure takes account in this variant of the position of the determined parameter of the current respiratory curve and the corresponding parameter of the reference respiratory curve relative to the reference recording time window. For example, it may be considered whether the parameter lies in or outside the reference recording time window with regard to the current and reference respiratory curve or how large the spacing is at the respective start and/or end point of the reference recording time window. By this, it may be derived directly whether and how the current respiratory curve has been changed or displaced in relation to the desired respiration state.

Particularly advantageously, the disclosure is configured also to include acquiring a current value of the current respiratory curve and comparing it with the trigger threshold value. This procedure substantially corresponds to the establishing of the time point at which an individual scan of the magnetic resonance scan is started. By a movement in addition to the respiratory motion, the following situations may arise.

In one situation, the current respiratory curve no longer reaches the original trigger threshold value defined on the reference respiratory curve. Consequently, no or no further individual scan is started automatically.

In a second situation, the current respiratory curve reaches the trigger threshold value, but this no longer corresponds to the temporal start point of the reference recording time window. An individual scan is then automatically stared, but potentially partially covers undesirable respiratory states.

In a third situation, the current respiratory curve reaches the trigger threshold value, and this also still corresponds (e.g., substantially) to the temporal start point of the reference recording time window. An individual scan is then started automatically, although it does not image the recording region of the patient under examination, because due to the unforeseen movement, the patient has assumed a changed position relative to his original position. In other words, in this case, the wrong recording region is imaged.

Including the comparison of at least one parameter of the current respiratory curve, as set out by reference to the preceding embodiments, it may now advantageously be decided which of the defined situations exists. Based thereon, an appropriate correcting mechanism may be started.

Accordingly, in one embodiment, the method includes acquiring a reference respiratory curve of the patient over a plurality of respiratory cycles, establishing a respiration state of the patient that is suitable for the magnetic resonance scan based on the reference respiratory curve, and determining at least one reference recording time window and a trigger threshold value for starting a magnetic resonance scan based on the previously determined respiration state. These method acts are repeated if a current value of the current respiratory curve does not reach the trigger threshold value over a respiratory cycle. This procedure addresses, in particular, the initially cited of the alternative situations. By a movement of the patient, the current respiratory curve has here become (e.g., severely) displaced relative to the reference respiratory curve such that the trigger threshold value is not achieved. In this case, a "relearning" of the respiration state, the reference recording time window and/or the trigger threshold values takes place. The magnetic resonance scan is interrupted for this. The relearning takes place based on a reference respiratory curve, in other words, a plurality of reference respiratory cycles which are used for determining respiratory states, reference recording time window and/or trigger threshold value is again acquired. Thus, in this exemplary embodiment, current and reference respiratory curves are interleaved with one another. The repetition of the aforementioned acts may be carried out dependent upon patient movement occurring outside the respiratory motion as often as needed within a magnetic resonance scan.

A relearning of the reference recording time window and/or the trigger threshold value may also take place when a deviation between at least one monitored parameter of the current respiratory curve and the corresponding parameter is greater than a previously defined first tolerance threshold value, specifically regardless of whether the trigger threshold value is achieved or not. Thus, a relearning of the reference recording time window and/or the trigger threshold value are also provided when at least one parameter of the current respiratory curve deviates too severely from the corresponding parameter. Thereby, the other two situations are also addressed. The first tolerance threshold value may be stored before the magnetic resonance scan for each of the possible parameters, for example, in a memory unit of a computation unit. The tolerance threshold value may be determined manually or automatically. It may depend, in particular, on the type of the magnetic resonance scan or the specific anatomy of the patient or may be specified by default setting.

It is particularly advantageous that the determination of the trigger threshold value is carried out taking account of the current patient position, that is, the position caused by the movement.

In another embodiment, magnetic resonance data that has been acquired in the reference recording time window of a respiratory cycle run through before the current respiratory cycle of the current respiratory curve, is at least partially discarded if a deviation between at least one monitored parameter of the current respiratory curve and the corresponding parameter is greater than a previously defined second tolerance threshold value. Through the continuous acquisition of the current respiratory curve and the continuous monitoring of at least one of its parameters associated therewith, it may be recognized when an unforeseen movement impairs at least one already started individual scan. The disclosure thus permits the decision with respect to discarding magnetic resonance data of at least this individual scan retrospectively after its completion. If, for each respiratory cycle of the current respiratory curve, only an individual scan is carried out in the reference recording window, its scan data may be discarded. If, for each respiratory cycle of the current respiratory curve a plurality of individual scans is carried out sequentially within the reference recording time window, based on the at least one monitored parameter, it may be decided for which individual scans the scan data are discarded. The second tolerance threshold value which represents a minimum measure for a quality of the scan data of the individual scans serves for this decision. The second tolerance threshold value may also be stored before the magnetic resonance scan for each of the possible parameters, for example, in a memory unit of a computation unit. The second tolerance threshold value may be determined manually or automatically. It may depend, in particular, on the type of magnetic resonance scan or the specific anatomy of the patient or may be specified by default setting. In particular, the second tolerance threshold value may be identical to the first tolerance threshold value.

In an advantageous embodiment, after a discarding of scan data for at least one individual scan, the individual scan may be repeated automatically in one of the subsequent respiratory cycles of the current respiratory curve, in particular, after a relearning of the reference recording time window and/or the trigger threshold value.

In another particularly advantageous embodiment, magnetic resonance data that has been acquired in the reference recording time window of a respiratory cycle run through before the current respiratory cycle of the current respiratory curve is retained although a deviation between at least one monitored parameter of the current respiratory curve and the corresponding parameter is greater than a previously defined second tolerance threshold value. However, this occurs only if the magnetic resonance scanning takes place with contrast medium administration and/or the magnetic resonance scanning is substantially completed at the time point of the ascertainment of the deviation. This embodiment variant advantageously takes into account that it may be uneconomical to repeat individual scans (and, if relevant relearning them) if the overall scan has already been carried out almost completely on occurrence of the unforeseen movement, because each repetition prolongs the examination duration and therefore the occupancy duration of the medical imaging system. The proportion of a magnetic resonance scan that suffices to prevent a discarding of scan data may depend on the type of magnetic resonance scan, the patient or the occupancy plan or capacity usage of the medical imaging system employed (e.g., between 80% and 100%, or 85%, 90%, or 95%). Alternatively, and/or additionally, this embodiment variant also considers that there are magnetic resonance scans which cannot be repeated without difficulty. This includes, in particular, scans using a contrast medium, because a maximum contrast medium dose must not be exceeded for the patient. At the same time, a scan data acquisition with contrast medium takes place triggered or dependent upon the administration time point in order to achieve a best possible image contrast. This may not be achieved on repetition of an individual scan.

In the event that the deviation between a monitored parameter of the current respiratory curve and the corresponding parameter exceeds the second tolerance threshold value, it may even advantageously also be provided to prevent the relearning of the reference recording time window and the trigger threshold value with regard to the curve shape changed by the movement.

From the user standpoint, it is particularly advantageous if the current respiratory curve is displayed for a user. In particular, the course of the current respiratory curve is displayed. This enables a user to perform visual monitoring of the current respiratory curve directly during the scan. For this purpose, it is particularly advantageous if the display takes place directly in the examination space or a monitoring/operating center for controlling a medical imaging system. The display may take place on a display unit of the medical imaging system itself. Besides the shape of the current respiratory curve, overlaid thereon, the reference recording time window and/or the trigger threshold value and/or the position of individual scans relative to the current respiratory curve may be represented.

In a further aspect, the present disclosure relates to a computation unit for monitoring a current respiratory curve of a patient with regard to a recording region which is imaged by magnetic resonance scanning. This computation unit is configured to: acquire a reference respiratory curve of the patient over a plurality of respiratory cycles; establish a respiration state of the patient that is suitable for the magnetic resonance scanning based on the reference respiratory curve; determine at least one reference recording time window and a trigger threshold value for starting a magnetic resonance scan based on the previously determined respiration state; and continuously acquire and monitor a current respiratory curve during the magnetic resonance scanning in the recording time window.

In one embodiment, the computation unit is linked to a medical imaging system such that control signals or data for carrying out a repetition of an individual scan of a magnetic resonance scan or patient-specific information and/or information characterizing a magnetic resonance scan may be transferred. Furthermore, a signal of the current respiratory curve that is able to be represented may be transferred to the medical imaging system for display. The computation unit may also be linked directly to a display unit of a medical imaging system for display of the current respiratory curve.

Advantageously, the computation unit is integrated into the medical imaging system. Alternatively, the computation unit may also be arranged separately or remotely therefrom. The computation unit may be configured, in particular to carry out the act of continuous monitoring of the current respiratory curve, but also the entire method, for a medical imaging system or for a plurality of systems, e.g. in a radiology center or hospital having a plurality of magnetic resonance systems.

A further aspect relates to a system for monitoring a current respiratory curve of a patient with regard to a recording region that is imaged by magnetic resonance scanning, including a computation unit and a sensor unit for acquiring a reference respiratory curve and/or a current respiratory curve of a patient, wherein the computation unit and the sensor unit are linked for data exchange. The acquisition includes the detection of the respiratory curve. The sensor unit is configured to detect the body motion caused by respiration before, during, between and after individual scans of a magnetic resonance scan. For this purpose, the sensor unit is arranged close to or directly on the body of the patient. The sensor unit may be configured in the form of one of the following sensors or sensor types: respiratory sensor in the form of an oscillator circuit arranged in a local coil, for example, for detecting voltage changes caused by movement, respiratory sensor in the form of a chest belt for detecting pressure and/or tension changes, respiratory sensor in the form of an optical marker on the body of the patient, whose position change is recorded by camera monitoring, or suchlike.

In a further aspect, the present disclosure relates to a medical imaging system for monitoring a current respiratory curve of a patient with regard to a recording region which is imaged by magnetic resonance scanning, including a computation unit and a sensor unit for acquiring a reference respiratory curve and/or the current respiratory curve of a patient. The medical imaging system may be configured as a magnetic resonance system. The computation unit may be physically connected to the medical imaging system or arranged integrated into it. Alternatively, the computation unit may also be arranged separately or remotely therefrom.

In a further aspect, the present disclosure relates to a computer program with program code for monitoring a current respiratory curve of a patient with regard to a recording region which is imaged by magnetic resonance scanning. The computer program, when executed on a computer, is configured to cause the computer or system to: acquire a reference respiratory curve of the patient over a plurality of respiratory cycles; establish a respiration state of the patient that is suitable for the magnetic resonance scanning based on the reference respiratory curve; determine at least one reference recording time window and a trigger threshold value for starting a magnetic resonance scan based on the previously determined respiration state; and continuously acquire and monitor a current respiratory curve during the magnetic resonance scanning in the recording time window.

In a further aspect, the present disclosure relates to a computer-readable data carrier with program code of a computer program for monitoring a current respiratory curve of a patient with regard to a recording region which is imaged by magnetic resonance scanning. The computer program, when executed on a computer, causes the computer or system to: acquire a reference respiratory curve of the patient over a plurality of respiratory cycles; establish a respiration state of the patient that is suitable for the magnetic resonance scanning based on the reference respiratory curve; determine at least one reference recording time window and a trigger threshold value for starting a magnetic resonance scan based on the previously determined respiration state; and continuously acquire and monitor a current respiratory curve during the magnetic resonance scanning in the recording time window.

Advantageously, the continuous monitoring of the current respiratory curve of the patient may be carried out on a computer, for example, in a computation unit of a medical imaging system.

The performance of the disclosure in the form of a computer program or a computer-readable data carrier including program code of a computer program offers the advantage that existing computer systems or computation units may be configured by a software update in order to achieve a function according to the disclosure.

The computer program may alternatively be configured in the form of a computer program product and have additional units. These may be configured as hardware, for example, as a storage medium on which the computer program is stored, and/or a hardware key in order to be able to use the computer program. Alternatively, or additionally, they may be configured as software, for example, as a program documentation or a software key, in order to be able to use the computer program.

BRIEF DESCRIPTION OF THE DRAWINGS

The above-described properties, features, and advantages of this disclosure and the manner in which these are achieved will now be described in detail, more clearly and explicitly with the following description of the exemplary embodiments, and by reference to the drawings. This description entails no limitation of the disclosure to these exemplary embodiments. In different figures, the same components are provided with identical reference signs. The drawings are not to scale. In the drawings.

DETAILED DESCRIPTION

Figure 1:
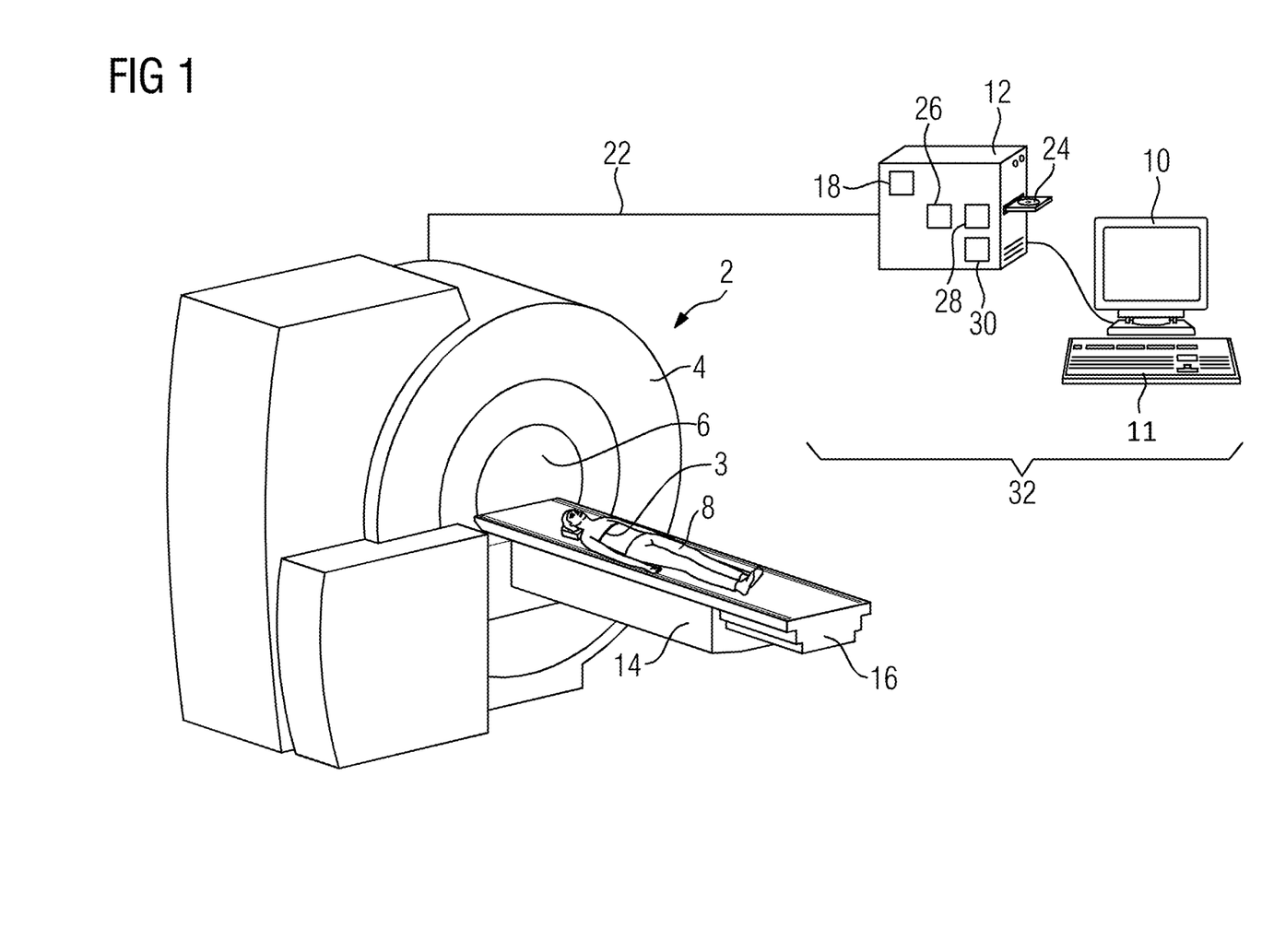
FIG. 1 depicts a perspective view of a medical imaging system in the form of a magnetic resonance system according to an exemplary embodiment.

The medical imaging system 2 shown in FIG. 1 in the form of a magnetic resonance system includes a hollow cylindrical-shaped base unit 4 in the interior of which during operation, the so-called tunnel 6, an electromagnetic field is generated for a magnetic resonance scanning or investigation of an examination object in the form of a patient 8.

Additionally, a patient table 14 with a movable support board 16 is provided. The patient 8 may be positioned, as shown, on the support board 16. The patient table 14 is positioned outside the base unit 4 so that the support board 16 together with the patient 8 may be moved at least partially into the tunnel 6 for the examination. In this embodiment, a sensor unit 3 in the form of a chest belt is attached to the patient 8 at chest height. The chest belt 3 serves to acquire a respiratory curve A of the patient 8, in particular a reference respiratory curve REFA and a current respiratory curve AKA.

The tomograph 2 has a computation unit 12 in the form of a computer system which is configured as a computer and is linked to a display unit 10, for example, for graphical display of a current respiratory curve AKA, and an input unit 11. The display unit 10 may be, for example, an LCD, plasma, or OLED screen. It may also be a touch-sensitive screen which is configured as an input unit 11. Such a touch-sensitive screen may be integrated into the imaging device or may be configured as part of a mobile device. The input unit 11 is, for example, a keyboard, a mouse, a so-called touch-sensitive screen or a microphone for speech input. The input unit 11 may also be configured to recognize movements of a user and to convert them into corresponding commands.

Figure 2:
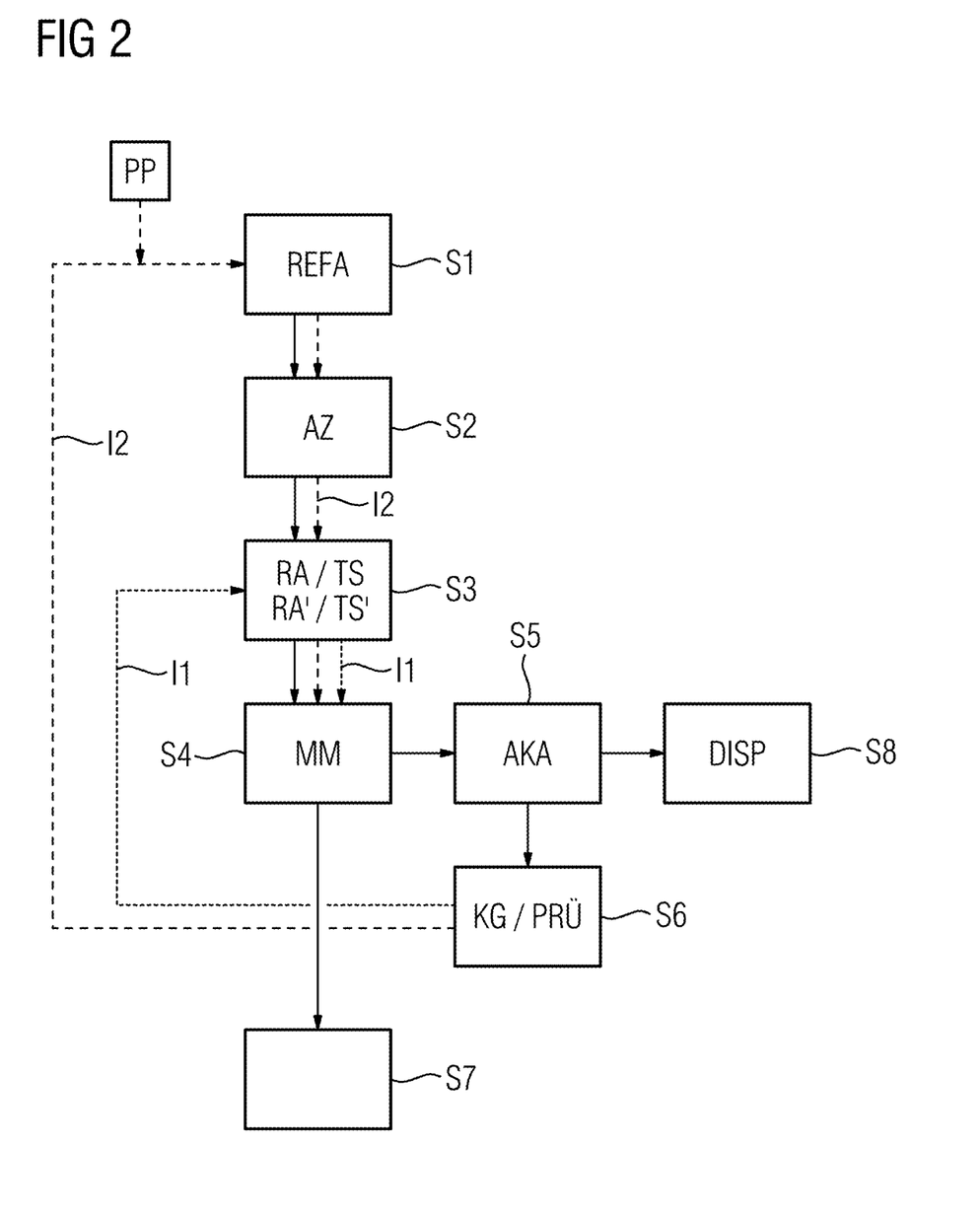
FIG. 2 depicts a schematic representation of a method according to an exemplary embodiment.

The computer system 12 is configured to carry out a method as described in greater detail, for example, by reference to FIG. 2. For this purpose, the computer system 12 is linked to the base unit 4 of the tomograph 2 for data exchange. For example, control signals for the tomograph 2 for a repetition of at least one individual scan of an examination may be transferred from the computer system 12 to the base unit 4 or control signals may be transferred according to the determined trigger threshold value TS and the determined reference recording time window RA. The driving of the base unit 4 takes place according to a scan protocol selected according to the individual scan. On the other hand, commands for discarding scan data of particular individual scans are transferred to the base unit 4. The connection 22 is realized via corresponding interfaces cable-bound or cable-free in a known manner. The connection 22 may also be used in order to realize a data exchange between the computer system 12 and the sensor unit 3 and to transfer data relating to the shape of the acquired respiratory curve to the computer system 12. Alternatively, particularly if the sensor unit 3 is not included by the medical imaging system 2, a further and similarly configured link may be provided for this data exchange. The sensor unit 3 and the computation unit 12 together form a system 32.

The computer system 12 includes an acquisition and transfer unit 26 in the form of a data interface. This is configured, based on the connection 22 to the magnetic resonance system 2 or a comparable connection to the sensor unit 3, to acquire scan data relating to a patient movement, for example a respiratory curve of the patient. In particular, the acquisition unit 26 is configured to acquire a reference respiratory curve REFA and a current respiratory curve AKA of the patient 8, in each case over individual, or a plurality of, respiratory cycles. The acquisition unit 26 may be configured as a hardware or a software interface, for example, as a PCI bus, USB, or Firewire. A data exchange by the connections mentioned may take place using a network connection. The network may be configured as a "Local Area Network" (LAN), for example, as an Intranet or as a "Wide Area Network" (WAN). The network connection may be formed cable-free, for example, as a wireless LAN (WLAN or Wi-Fi). The network may also include a combination of different network types.

The computer system 12 further includes an establishing unit 28 which serves and is configured to establish a respiration state AZ suitable for the magnetic resonance scan, based on the reference respiratory curve. For example, the establishing unit 28 determines in which region within the reference respiratory curve per respiratory cycle the respiration state the complete exhalation is situated. For this purpose, the establishing unit 28 may monitor and evaluate the shape and/or the characteristic parameters of the respiratory curve over the plurality of respiratory cycles of the reference respiratory curve. Information regarding the (planned) magnetic resonance scan may be included in the establishing of the suitable respiration state AZ, for example, the planned duration or the structure of the scans (e.g., individual scan or sequential scanning). Furthermore, the establishing unit may take account of information regarding the patient himself, for example, whether irregular respiration exists even during rest. The further information may be retrievably stored in a memory store 18 of the computation unit 12. The memory store 18 may be configured, for example, as a "Random Access Memory" (RAM), as a permanent mass storage (e.g., hard drive, solid state disk) or the like. The first and/or second tolerance threshold value may further be retrievably stored in the memory store 18.

The computer system 12 also includes a determining unit 30 configured to determine at least one reference recording time window RA and a trigger threshold value TS to start the magnetic resonance scan within the current respiratory curve AKA based on the previously determined respiration state AZ. For this purpose, in particular, the value (e.g., averaged over the plurality of respiratory cycles) of the reference respiratory curve REFA may be specified at the start of the desired respiration state AZ as the trigger threshold value TS. Furthermore, in particular, the duration (e.g., averaged over the plurality of respiratory cycles) of the desired respiration state AZ may be specified as the reference recording time window RA. The determining unit 30 may further be configured to transfer the determined trigger threshold value TS and the reference recording time window RA into corresponding control signals for the base unit 4 in order thereby subsequently to carry out the at least one magnetic resonance scan within the reference recording time window RA of the current respiratory curve using the trigger threshold value TS.

The acquisition and transfer unit 26 is also configured accordingly to transfer the trigger threshold value TS and the reference recording time window RA or corresponding control signals for further processing by the link 22 to the base unit 4.

The acquisition and transfer unit 26 is further configured further to acquire the current respiratory curve AKA continuously, subsequently to the reference respiratory curve REFA, in particular, during the magnetic resonance scan in the reference recording time window RA and to monitor it continuously, as described in greater detail below in relation to FIG. 2.

In the present case, in particular, the cited units 26, 28, and 30 are configured as separate modules within the computer system 12 which, where required, exchange data with one another. Alternatively, all the units named may be integrated as a computation unit, whether in the form of a physical or a functional integrity.

In particular, the units 26, 28, and 30 may be configured in the form of a hardware or software component. For example, the units are configured as a microprocessor, as Field Programmable Gate Arrays (FPGAs) or include an arithmetic logic unit.

The computer system 12 may cooperate with a computer-readable data carrier 24, in particular, in order to carry out a method by a computer program with program code. Furthermore, the computer program may be retrievably stored on the machine-readable carrier 24. In particular, the machine-readable carrier 24 may be a CD, DVD, Blu-Ray disk, a memory stick, or a hard disk drive.

At least one computer program which carries out all the method acts of the method when the computer program is carried out on the computer 12 may be stored on the memory store 18 of the computer system 12. The computer program for carrying out the method acts of the method includes program code. Furthermore, the computer program may be configured as an executable file and/or may be stored on a computer system other than the computer system 12. For example, the magnetic resonance tomography system 2 may be configured so that the computer system 12 loads the computer program for carrying out the method via an Intranet or the Internet into its internal working memory. Alternatively, it may be provided that the computer system 12 is itself part of an Internet or Intranet, for example, of Hospital Information System (HIS) or a Radiology Information System (RIS) and has access to different magnetic resonance tomography systems of the institution in order to carry out the method centrally for different tomographs.

FIG. 2 shows a schematic representation of a method according to an exemplary embodiment. The method includes a plurality of acts. In act S1 of the method, the acquisition of a reference respiratory curve REFA of a patient 8 takes place over a plurality of respiratory cycles. During the acquisition of the reference respiratory curve REFA, (as yet) no magnetic resonance scan takes place. The acquisition takes place by a sensor unit 3, for example, of a respiratory sensor attached to the chest of the patient 8, or by a computation unit 12. The reference respiratory curve REFA advantageously represents the respiratory motion of the patient 8 within the recording region, that is, of the body region that is to be imaged by magnetic resonance scanning. The recording takes place over a plurality of respiratory cycles (including a complete exhalation and a complete inhalation). The reference respiratory curve may have a regularity of shape between the respiratory cycles. This regularity is subsequently utilized. The shape of the acquired reference respiratory curve REFA is specific for the patient, for the arrangement of the sensor unit 3 relative to the patient 8 and for the type of sensor unit 3.

In act S2, at least one respiration state AZ that is suitable for a magnetic resonance scan is determined for the patient based on the reference respiratory curve REFA.

The establishment of the respiration state AZ includes, in particular, an establishment of a temporal duration and/or a position of the respiration state relative to the specific reference respiratory curve REFA of the patient 8. The respiration state may be the state of complete exhalation, because this corresponds to the longest respiration state and is therefore particularly well suited for magnetic resonance scans. Alternatively, a plurality of respiratory states may be determined. In particular, a plurality of respiratory states may be considered together for a magnetic resonance scan. For example, the respiration state of complete exhalation per respiration cycle may include the region of the reference respiratory curve in which the value of the respiratory curve (on average over all the respiratory cycles acquired) lies below twenty percent of the averaged maximum value. Alternative definition rules for establishing a respiration state may equally be used. They depend, in particular, on the type of the respiration state.

In act S3, a determination of at least one reference recording time window RA and of a trigger threshold value TS takes place, based on the established respiration state AZ. The reference recording time window RA may correspond to the region of the respiration state AZ per respiratory cycle, but may also be offset therefrom, in particular, temporally delayed therefrom on the reference respiratory curve REFA. The reference recording window REFA may be temporally interrupted in the sense that each sub-portion may be provided for a sequential individual scan of the magnetic resonance scan or may represent a coherent time window. The trigger threshold value TS is determined, for example, as the value (e.g., averaged over all the acquired respiratory cycles) that the reference respiratory curve assumes at the start of the reference recording window RA or each sub-individual recording window.

Figure 3:
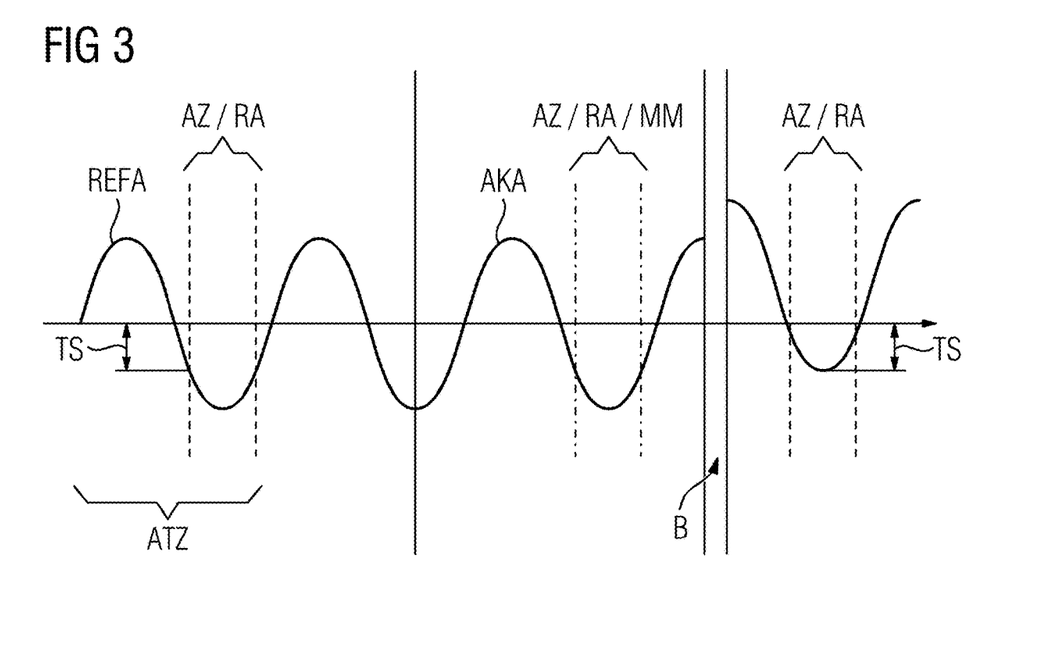
FIG. 3 depicts a schematic representation of a respiratory curve including a reference respiratory curve and a current respiratory curve according to an exemplary embodiment.

A reference respiratory curve REFA together with the respiration state AZ suitable for the magnetic resonance scanning and the reference recording time window RA and the trigger threshold value TS is shown, by way of example, in FIG. 3. A complete respiratory cycle ATZ is also shown. A plurality of respiratory cycles, (e.g., three to five respiratory cycles), is included in the reference respiratory curve (represented here by the dashed line). The reference respiratory curve REFA extends as far as the dot-dashed separating line and transitions without interruption into the current respiratory curve AKA. The reference respiratory curve REFA and the current respiratory curve AKA together form the respiratory curve AK of the patient 8.

In act S4, at least one magnetic resonance scan MM is performed within the determined reference recording time window RA of the current respiratory curve AKA. In other words, the reference recording time window RA and the trigger threshold value TS are transferred to the current respiratory curve AKA, in particular, to each individual respiratory cycle ATZ of the current respiratory curve AKA. This procedure assumes that the shape of the current respiratory curve AKA does not differ on average over a plurality of respiratory cycles ATZ from the shape of the reference respiratory curve REFA. In this way, it is provided that the magnetic resonance data generated all corresponds to the same respiration state AZ of the patient 8.

At least simultaneously with act S4, that is, in parallel with the magnetic resonance scan, in act S5, a continuous acquisition of the current respiratory curve AKA takes place. Particularly advantageously, it may be provided also to acquire and monitor the current respiratory curve AKA outside the reference recording time window RA, once the determination of the reference recording time window RA and the trigger threshold value TS have been completed. This procedure is based upon the recognition that in addition to the substantially regular respiratory motion, an additional unexpected and, in particular, single patient movement may occur, which leads to a change/displacement of the current respiratory curve AKA. This change/displacement may impair the magnetic resonance scan or individual scans which, according to the scan protocol, are provided for subsequent respiratory cycles ATZ of the current respiratory curve AKA. Through the continuous monitoring, deviations of the curve shape may be recognized early and faulty scans may be prevented.

Accordingly, in act S6, an establishment of at least one parameter KG characterizing the current respiratory curve AKA takes place. The parameter KG is, in particular, characteristic for the shape of the current respiratory curve AKA. Advantageously, not only one parameter KG is established, but rather a plurality of parameters KG. These allow a more exact analysis of whether or how or how strongly the current respiratory curve AKA deviates from the reference respiratory curve. Possible parameters KG are, for example, the position of at least one turning point of the current respiratory curve, a temporal spacing of two successive turning points of the current respiratory curve, a spacing between minimal and maximal deflection of a respiratory cycle of the current respiratory curve, the gradient and/or the constancy of the current respiratory curve. This list is not exhaustive and other parameters KG may also be suitable and included by the disclosure.

Act S6 may also include a checking act PRU in which the at least one established parameter KG of the current respiratory curve AKA is checked for matching with the corresponding parameter of the reference respiratory curve REFA. Alternatively, or additionally, if at least one established parameter KG of the current respiratory curve AKA relates to only one respiratory cycle of the current respiratory curve AKA, the checking act may also take place with regard to matching with the corresponding parameter of a second respiratory cycle of the current respiratory curve AKA. Thus, a derivation of a parameter KG also takes place using the reference respiratory curve REFA. This procedure permits a hardly delayed, that is, effectively instant assessment of how great the deviations between the curve shape of the reference and actual respiratory curves REFA, AKA are.

Act S6 also includes a continuous monitoring of the value of the current respiratory curve AKA as compared with the trigger threshold value. If the threshold value has been reached and if there are further parameter deviations within a first, parameter-specific tolerance threshold value S1, the shape is unchanged between the current and the reference respiratory curves. For each further respiratory cycle ATZ of the current respiratory curve AKA, the magnetic resonance scan MM is automatically continued within the reference recording time window RA, making use of the trigger threshold value TS, as is illustrated by the iteration loop I1.

An unforeseen patient movement B may now provide that the original trigger threshold value TS defined by the reference respiratory curve REFA is no longer reached, as illustrated in FIG. 3 (right side). Consequently, no further magnetic resonance scan MM is automatically started.

Figure 4:
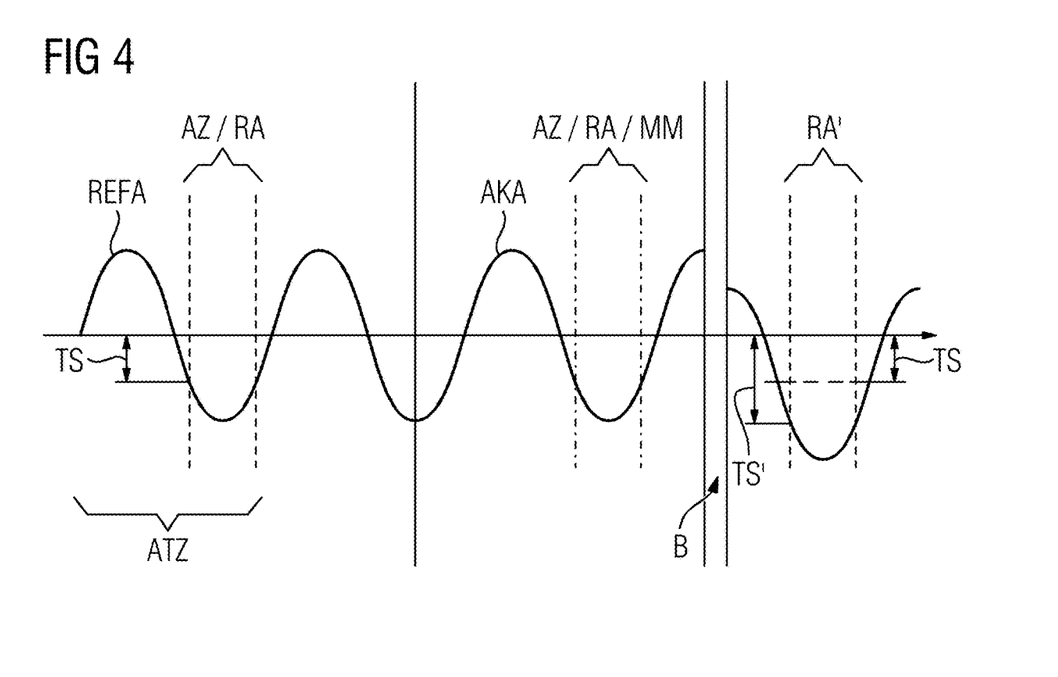
FIG. 4 depicts a schematic representation of a reference respiratory curve according to a further exemplary embodiment.

The patient movement B may also provide that although the current respiratory curve AKA reaches the trigger threshold value TS, it no longer represents the temporal start point of the reference recording time window TS, as illustrated in FIG. 4 (right side). An individual scan would then be started automatically, but potentially at least partially also covers undesirable respiration states.

The patient movement B may also provide that the current respiratory curve AKA reaches the trigger threshold value TS and also represents the temporal start point of the reference recording time window RA. An individual scan would here also be started automatically, although it would not image the recording region of the patient under examination, if due to the movement B, the patient 8 has assumed a changed position relative to his original position.

If the continuous monitoring in act S6 now results therein that the current respiratory curve AKA does not reach the trigger threshold value TS over a complete respiratory cycle and/or that at least one monitored parameter KG of the current respiratory curve AKA lies outside the first tolerance threshold value S1, a relearning is initiated according to the iteration loop 12. In this regard, the acts S1, S2, S3 are repeated while interrupting the magnetic resonance scan MM in order to determine a reference recording time window RA' configured to the current respiratory curve AKA changed by the movement and a corresponding trigger threshold value TS'. Because the current respiratory curve AKA after a patient movement B may be, inter alia, specific for the current patient position the current patient position is advantageously considered in the determination of the adapted reference recording time window RA' and of the corresponding trigger threshold value TS'. After completion of the relearning, the magnetic resonance scan MM and the continuous acquisition and monitoring of the current respiratory curve AKA are continued.

In particular, if a patient movement B takes place during a magnetic resonance scan MM or an individual scan, that is, as magnetic resonance data is just being acquired, in a further act S7, in the context of the subsequent respiratory cycle ATZ, it may be tested whether at least one parameter deviation lies outside a second, parameter-specific tolerance threshold value S2. The tolerance threshold value S2 may be retrievably stored in the memory store 18. In particular, the tolerance threshold value S2 may correspond to the tolerance threshold value S1. If this is the case, the magnetic resonance data of the previous respiratory cycle may be discarded as erroneous or qualitatively inferior. In a subsequent respiratory cycle, if relevant, after a determination of a suitable reference recording time window RA' and of the corresponding trigger threshold value TS', the magnetic resonance scan or the individual scan may be repeated automatically in order to generate improved magnetic resonance data.

In the case, in particular, in which according to the scan protocol, a plurality of sequential individual scans are provided within a respiratory cycle, it may be provided to carry out the checking for each individual scan separately and also only to discard the individual magnetic resonance data for those subregions of the reference recording time window for which the parameter deviation lies outside the tolerance.

In act S7, it may further be considered whether the magnetic resonance scan has been carried out with the administration of contrast medium or whether, at the onset of the patient movement, the magnetic resonance scan MM was substantially, for example, 90 or 95 percent complete. In such situations, the scan data is not discarded in favor of an effective time management of the medical device and/or to protect the patient, even if a parameter deviation lies above the second tolerance threshold value S2. In particular, in such situations, no relearning is initiated, for known reasons, although a parameter deviation may also lie above the first tolerance threshold S1 in such cases.

In a further act S8, the current respiratory curve AKA is displayed for a user, for example, on the display unit 10. For example, two or three respiratory cycles ATZ may be displayed in parallel. In this way, the user may realize visually current deviations of the current respiratory cycle ATZ instantaneously. Above the respiratory curve, the reference recording time window and/or the start and end point of the magnetic resonance scanning and, in particular, of individual scans according to the scan protocol may be displayed within a respiratory cycle.

Where it has not yet explicitly been set out, although useful and in the spirit of the disclosure, individual exemplary embodiments, individual sub-aspects or features thereof may be combined or exchanged with one another without departing from the scope of the present disclosure. Advantages of the disclosure described in relation to an exemplary embodiment also apply without explicit mention, where transferable, to other exemplary embodiments.

In summary, a continuous acquisition and analysis of a respiratory curve may detect falsely set scan regions. If it is ascertained following the recording of a scan region that a trigger threshold value does not (any longer) correspond to the desired respiration state, a relearning may be instigated. Scans which have been made with an erroneous trigger threshold value, may be discarded automatically and repeated with a newly learned trigger threshold value. Furthermore, the disclosure enables it to be decided automatically to discard magnetic resonance data which represents the desired respiration state but lies at a significantly different position due to movement, and to scan it anew. In the case of segmented/sequential scans (e.g., TSE MultiSlice recordings), only particular scan data may be determined for a new recording.

Although the disclosure was illustrated and described in more detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for monitoring a current respiratory curve of a patient comprising at least one recording region configured to be imaged by magnetic resonance scanning, the method comprising:
  acquiring a reference respiratory curve of the patient over a plurality of respiratory cycles, wherein the reference respiratory curve follows or is followed by the current respiratory curve;
  establishing a respiration state of the patient suitable for the magnetic resonance scanning based on the reference respiratory curve;
  determining at least one reference recording time window and a trigger threshold value for starting a magnetic resonance scan based on the established respiration state, wherein the magnetic resonance scan is configured to measure the current respiratory curve, and wherein the trigger threshold value corresponds to a value of the reference respiratory curve at a start point of the at least one reference recording time window;
  carrying out the magnetic resonance scan within the determined at least one reference recording time window of the current respiratory curve using the trigger threshold value;
  continually further acquiring and monitoring the current respiratory curve during the magnetic resonance scan in the determined at least one reference recording time window;
  identifying that: (1) a current value of the current respiratory curve does not reach the trigger threshold value over a respiratory cycle, and/or (2) a deviation between at least one parameter of the current respiratory curve and a corresponding parameter of the reference respiratory curve is greater than a first tolerance threshold value; and
  repeating the acquiring of a new reference respiratory curve, the establishing of a new respiration state of the patient, and the determining of at least one new reference recording time window and a new trigger threshold value based on the identifying that (1) the current value of the current respiratory curve does not reach the trigger threshold value over the respiratory cycle, and/or (2) the deviation between the at least one parameter of the current respiratory curve and the corresponding parameter of the reference respiratory curve is greater than the first tolerance threshold value.

2. The method of claim 1, wherein the continuous monitoring of the current respiratory curve comprises establishing the at least one parameter of the current respiratory curve and checking for matching with the corresponding parameter of the reference respiratory curve.

3. The method of claim 2, wherein the at least one parameter of the current respiratory curve comprises: a position of at least one turning point of the current respiratory curve, a temporal spacing of two successive turning points of the current respiratory curve, a spacing between minimal and maximal deflection of a respiratory cycle of the current respiratory curve, a gradient of the current respiratory curve, a constancy of the current respiratory curve, or a combination thereof.

4. The method of claim 1, wherein the continuous monitoring of the current respiratory curve comprises establishing at least one parameter characteristic for a first respiratory cycle of the current respiratory curve and checking for matching with a corresponding parameter of a second respiratory cycle of the current respiratory curve.

5. The method of claim 4, wherein the at least one parameter of the current respiratory curve comprises: a position of at least one turning point of the current respiratory curve, a temporal spacing of two successive turning points of the current respiratory curve, a spacing between minimal and maximal deflection of a respiratory cycle of the current respiratory curve, a gradient of the current respiratory curve, a constancy of the current respiratory curve, or a combination thereof.

6. The method of claim 1, wherein the continuous monitoring comprises acquiring the current value of the current respiratory curve and comparing the current value with the trigger threshold value.

7. The method of claim 1, wherein the determination of the trigger threshold value takes account of a current patient position.

8. The method of claim 1, wherein magnetic resonance data acquired in the at least one reference recording time window of a respiratory cycle run through before a current respiratory cycle of the current respiratory curve is at least partially discarded when the deviation between the at least one parameter of the current respiratory curve and the corresponding parameter of the reference respiratory curve is greater than the first tolerance threshold value.

9. The method of claim 1, wherein magnetic resonance data acquired in the at least one reference recording time window of a respiratory cycle run through before a current respiratory cycle of the current respiratory curve is retained, although the deviation between the at least one parameter of the current respiratory curve and the corresponding parameter of the reference respiratory curve is greater than the first tolerance threshold value, when the magnetic resonance scan takes place with contrast medium administration or the magnetic resonance scan is completed at a time point of ascertainment of the deviation.

10. The method of claim 1, further comprising: displaying the current respiratory curve.

11. The method of claim 1, wherein the magnetic resonance scan is carried out within the determined at least one reference recording time window of the current respiratory curve instantly upon reaching the trigger threshold value or with a further temporal offset from reaching the trigger threshold value.

12. The method of claim 1, wherein the trigger threshold value further corresponds to a value of the reference respiratory curve at an end point of the at least one reference recording time window.

13. The method of claim 1, wherein the identifying comprises an identification that the current value of the current respiratory curve does not reach the trigger threshold value over the respiratory cycle, and
wherein the repeating of the acquiring, the establishing, and the determining is based on the identification that the current value of the current respiratory curve does not reach the trigger threshold value over the respiratory cycle.

14. The method of claim 1, wherein the identifying comprises an identification that the deviation between the at least one parameter of the current respiratory curve and the corresponding parameter of the reference respiratory curve is greater than the first tolerance threshold value, and
wherein the repeating of the acquiring, the establishing, and the determining is based on the identification that the deviation between the at least one parameter of the current respiratory curve and the corresponding parameter of the reference respiratory curve is greater than the first tolerance threshold value.

15. A system for monitoring a current respiratory curve of a patient comprising at least one recording region configured to be imaged by magnetic resonance scanning, the system comprising:
a sensor unit configured to acquire a reference respiratory curve, the current respiratory curve, or a combination thereof, wherein the reference respiratory curve follows or is followed by the current respiratory curve; and
a computer comprising a memory, wherein the computer is configured, with the memory, to:
establish a respiration state of the patient suitable for the magnetic resonance scanning based on the reference respiratory curve;
determine at least one reference recording time window and a trigger threshold value for starting a magnetic resonance scan based on the established respiration state, wherein the magnetic resonance scan is configured to measure the current respiratory curve, and wherein the trigger threshold value corresponds to a value of the reference respiratory curve at a start point of the at least one reference recording time window;
continuously acquire and monitor the current respiratory curve during the magnetic resonance scanning in the at least one reference recording time window;
identify that: (1) a current value of the current respiratory curve does not reach the trigger threshold value over a respiratory cycle, and/or (2) a deviation between at least one parameter of the current respiratory curve and a corresponding parameter of the reference respiratory curve is greater than a first tolerance threshold value; and
repeat the acquiring of a new reference respiratory curve, the establishing of a new respiration state, and the determining of a new reference recording time window and a new trigger threshold value based on the identifying that (1) the current value of the current respiratory curve does not reach the trigger threshold value over the respiratory cycle, and/or (2) the deviation between the at least one parameter of the current respiratory curve and the corresponding parameter of the reference respiratory curve is greater than the first tolerance threshold value.

16. The system of claim 15, wherein the computer and the sensor unit are linked for data exchange.

17. A computer program stored in a non-transitory computer readable medium, wherein the computer program, when executed on a computer, is configured to cause the computer to:
acquire a reference respiratory curve of a patient over a plurality of respiratory cycles, wherein the reference respiratory curve follows or is followed by a current respiratory curve comprising at least one recording region configured to be imaged by magnetic resonance scanning;
establish a respiration state of the patient suitable for the magnetic resonance scanning based on the reference respiratory curve;
determine at least one reference recording time window and a trigger threshold value for starting a magnetic resonance scan based on the established respiration state, wherein the magnetic resonance scan is configured to measure the current respiratory curve, and wherein the trigger threshold value corresponds to a value of the reference respiratory curve at a start point of the at least one reference recording time window;
continuously acquire and monitor the current respiratory curve during the magnetic resonance scanning in the at least one reference recording time window;
identifying that: (1) a current value of the current respiratory curve does not reach the trigger threshold value over a respiratory cycle, and/or (2) a deviation between at least one parameter of the current respiratory curve and a corresponding parameter of the reference respiratory curve is greater than a first tolerance threshold value; and
repeating the acquiring of a new reference respiratory curve, the establishing of a new respiration state, and the determining of a new reference recording time window and a new trigger threshold value based on the identifying that (1) the current value of the current respiratory curve does not reach the trigger threshold value over the respiratory cycle, and/or (2) the deviation between the at least one parameter of the current respiratory curve and the corresponding parameter of the reference respiratory curve is greater than the first tolerance threshold value.

18. The computer program of claim 17, wherein a magnetic resonance scan is carried out within the determined at least one reference recording time window of the current respiratory curve upon reaching the trigger threshold value or with a further temporal offset from reaching the trigger threshold value.

* * * * *